(12) United States Patent
Schoeni et al.

(10) Patent No.: US 9,910,004 B2
(45) Date of Patent: Mar. 6, 2018

(54) METHOD FOR DETECTING THE FOAM BOUNDARY AND A RESPECTIVELY EQUIPPED APPARATUS

(71) Applicant: Tecan Trading AG, Mannedorf (CH)

(72) Inventors: Markus Schoeni, Nanikon (CH);
Philipp Ott, Steg im Tosstal (CH);
Lars Kamm, Schanis (CH); Paul Zbinden, Wolfhausen (CH)

(73) Assignee: TECAN TRADING AG, Mannedorf (CH)

( * ) Notice: Subject to any disclaimer, the term of this patent is extended or adjusted under 35 U.S.C. 154(b) by 0 days.

(21) Appl. No.: 15/168,399

(22) Filed: May 31, 2016

(65) Prior Publication Data
US 2016/0356737 A1 Dec. 8, 2016

(30) Foreign Application Priority Data
Jun. 2, 2015 (CH) .......................... 783/15

(51) Int. Cl.
*G01R 27/08* (2006.01)
*G01N 27/22* (2006.01)
(Continued)

(52) U.S. Cl.
CPC ......... *G01N 27/22* (2013.01); *G01F 23/0069* (2013.01); *G01F 23/265* (2013.01);
(Continued)

(58) Field of Classification Search
CPC ...... G01F 23/26; G01F 23/266; G01F 23/263; G01F 23/265; G01F 23/284;
(Continued)

(56) References Cited

U.S. PATENT DOCUMENTS

| 5,493,922 | A  | * | 2/1996 | Ramey | .................. | G01F 23/266 |
|---|---|---|---|---|---|---|
|  |  |  |  |  |  | 137/392 |
| 2006/0207322 | A1 | * | 9/2006 | Krufka | .................. | G01F 23/263 |
|  |  |  |  |  |  | 73/304 C |

(Continued)

*Primary Examiner* — Thang Le
(74) *Attorney, Agent, or Firm* — Notaro, Michalos & Zaccaria P.C.

(57) ABSTRACT

A capacitively operating apparatus (100) has a container, a probe (3) movable into and/or out of the container, an input signal generator connectable to the probe (3) to provide an input signal ($s_{in}(t)$) which produces at least one output signal ($s_{out}(t)$) in the probe (3), and a measuring apparatus (M) connectable to the probe (3) to tap the output signal ($s_{out}(t)$) from the probe (3), and wherein the probe (3) is periodically chargeable and dischargeable, the output signal ($s_{out}(t)$) corresponds to the time progression of a charging/discharging curve which is produced by the periodic charging and discharging of the probe (3). The apparatus (100) also includes a circuit module (10, 11) with two comparators for providing a first comparator output signal (PWM1) and a second comparator output signal (PWM2) from the output signal ($s_{out}(t)$) and to correlate them with one another.

16 Claims, 7 Drawing Sheets

(51) Int. Cl.
 *G01F 23/00* (2006.01)
 *G01F 23/26* (2006.01)
 *G01N 35/10* (2006.01)
 *G01N 1/10* (2006.01)

(52) U.S. Cl.
 CPC ............. *G01F 23/266* (2013.01); *G01N 1/10* (2013.01); *G01N 35/1011* (2013.01); *G01N 2035/1018* (2013.01)

(58) Field of Classification Search
 CPC ............. G01F 23/261; G01N 35/1009; G01N 35/1065; G01N 35/1011; G01R 27/26; G01R 27/2605
 USPC ....... 324/676, 677, 678, 681, 663, 664, 667, 324/671, 662
 See application file for complete search history.

(56) References Cited

U.S. PATENT DOCUMENTS

| | | | | |
|---|---|---|---|---|
| 2007/0144253 | A1* | 6/2007 | Kobayashi | G01F 23/28 73/304 C |
| 2010/0268490 | A1* | 10/2010 | Chang | G01F 23/266 702/55 |
| 2010/0301878 | A1* | 12/2010 | Armbruster | G01F 23/0061 324/676 |
| 2012/0242354 | A1* | 9/2012 | Cors | G01F 23/266 324/672 |
| 2014/0152326 | A1* | 6/2014 | Zuppiger | G01N 35/1011 324/663 |

\* cited by examiner

METHOD FOR DETECTING THE FOAM BOUNDARY AND A RESPECTIVELY EQUIPPED APPARATUS

The invention relates to a method for detecting a foam boundary in a container. The invention also relates to a respectively equipped apparatus.

BACKGROUND OF THE INVENTION

There are numerous laboratory systems and medical as well as pharmaceutical appliances which require precise pipetting operations in order to obtain satisfactory analytic precision. It is necessary for this purpose to precisely define the filling level in test tubes, titre plates and other liquid containers. There are also applications which are concerned with the detection of foam-liquid phase boundaries and gas-foam phase boundaries. The term phase boundary shall be used below both for transitions between gaseous and liquid media (gas-liquid phase boundary), for gas-foam phase boundaries, and also for transitions between different liquid media (foam-liquid phase boundary).

Such a determination of the phase boundary is particularly relevant concerning the automation of measurement or test sequences. The so-called determination of the filling level typically occurs by means of a detection of the liquid level, i.e. the position of the phase boundary between the air and the liquid is determined. This process is also known as "Liquid Level Detection" (LLD).

Various methods for determining the filling level are known from the prior art, which are based on different physical principles such as the detection of the light reflected by the surface of the liquid, or the measurement of electrical properties of the pipettes when they are brought into contact with the liquid. Since a gas and a liquid have distinctly different dielectric constants, the gas-liquid phase boundary can also be determined via a change in capacitance.

Liquid level detection is used in pipetting devices for example. In this case, the pipetting needle shall be immersed as little as possible into the liquid to be pipetted during suction with a pipette in order to keep contamination of the sample liquid as low as possible. During suction, the pipetting needle is therefore typically immersed only a few millimeters below the liquid level. It needs to be ensured however that the pipetting needle is immersed to a sufficiently far extent so that no air can be aspirated. During the suction process, the pipetting needle is then continuously moved along the decreasing liquid level so that it remains immersed to an equally deep extent in relation to the liquid level. After the suction, it can be calculated where the level of the gas-liquid phase boundary should be situated on the basis of the aspirated volume and the cross-sectional surface area of the liquid container. During the surfacing of the pipetting tip, a surfacing signal with the calculated position of the gas-liquid phase boundary can be compared in order to thus verify the pipetting process.

It is therefore desirable on the one hand to enable the positioning of the pipetting tip slightly beneath the liquid surface. On the other hand, the filling level can vary strongly from one liquid container to another, which is why the pipetting tip must be precisely positionable in large areas. It is therefore exceptionally important to enable the correct and definite detection of the liquid surface.

The reliability of the recognition of the liquid surface with the known methods is unsatisfactory in a number of cases, especially in the case of liquids which are susceptible to the formation of foam.

It is therefore important to enable distinguishing between foam and/or liquid contacting of a probe that can be advanced in a container (e.g. in form of a pipette).

Applications can also be considered in which only the detection of a foam boundary is concerned.

OBJECT OF THE INVENTION

It is therefore the object to provide a method for the detection of a foam boundary which operates reliably and offers high precision.

It is a further object of the invention to provide a method for a detection of the transition of the probe from foam to liquid.

It is a further object of the invention to provide respective apparatuses.

DISCLOSURE OF THE INVENTION

The technical object of the invention as identified above is achieved by a method whose features are disclosed in claim 1.

In particular, a method is concerned for detecting a foam boundary in a container of an apparatus by means of a capacitively operating measuring apparatus, comprising a probe which can be moved, wherein at least one output signal is processed by the measuring apparatus. The method comprises the following steps which are carried out during the performance of an upward or downward movement of the probe in the container;
a) performing a charging process by predetermining an input signal which produces a charging process on a measuring capacitance (also known as total capacitance), wherein said measuring capacitance is formed from the probe, the air, the foam and the liquid;
b) providing a charging signal which is produced during the charging process in the measuring capacitance, on a first comparator and on a second comparator, wherein the first comparator is designed to provide a first output signal if the charging signal reaches a first reference voltage, and wherein the second comparator is designed to provide a second output signal if the charging signal reaches a second reference voltage which is greater than the first reference voltage;
c) discharging the measuring capacitance;
d) repetition of the steps a) to c);
wherein the first output signal and the second output signal are correlated with one another within the scope of an evaluation process.

The detection of a gas-liquid boundary and a gas-foam boundary in a container of an apparatus is especially concerned, which comprises a substantially capacitively operating measuring apparatus which processes the charging signal of a measuring capacitance and recognises whether liquid or foam was touched.

By periodically charging and discharging of the measuring capacitance (i.e. by repeating the steps a) to c)), the first comparator outputs a first PWM signal (also known as comparator output signal) and the second comparator outputs a second PWM signal (also known as comparator output signal). PWM stands for pulse-width modulation.

The pulse widths of these two output signals are of interest, especially the change in the impulse widths of the output signals between surfaced and immersed probe. The change in the first output signal can be multiplied by a predetermined factor in such a way that the product, in the case of a purely capacitive behaviour of the medium, corresponds to the change in the second outputs signal. This is the case during immersion of the probe into a liquid which is somewhat well-conductive. If foam is situated on the liquid however, the liquid capacitance cannot be discharged completely in the case of a suitable selection of the discharge time as a result of the relatively high impedance of the foam. This leads to the consequence that during the subsequent charging process a return current flows into the basic capacitance during the subsequent charging process. The flow of a return current has an effect especially at the beginning of the charging curve. The impulse width change of the first output signal multiplied by the predetermined factor can thus decrease in comparison with the impulse width change of the second output signal. The impulse width change in comparison with the impulse width of the surfaced probe can thus even become negative. By providing a suitable selection of the discharge time and the basic capacitance it is thus possible to distinguish whether the probe is immersed in liquid or in foam.

An apparatus of the invention is formed as a substantially capacitively operating apparatus whose features are disclosed in the independent apparatus claims.

The apparatus of the invention comprises:

a container;

a probe which can be moved into the container and/or out of the container;

an input signal generator which is connectable to the probe in order to provide an input signal which produces a charging signal on a measuring capacitance from the probe, the air, the foam and the liquid;

a measuring apparatus which is connectable to the probe in order to tap the charging signal as an output signal on the probe.

The apparatus is characterized in that the measuring capacitance is periodically chargeable and dischargeable by the charging signal;

the charging signal corresponds to a charging/discharging curve which is produced by the periodically charging and discharging of the measuring capacitance;

it comprises a circuit module with two comparators which are formed to provide from the output signal (or the charging signal) a first output signal and a second output signal and to correlate them with one another.

Further details are disclosed in the respective dependent claims.

Advantageous Effects

The most important advantage of the invention is that during the feed motion of a probe (e.g. in form of a pipette or needle) a foam boundary can be detected in a highly reliable and precise manner. It can thus be ensured that a respectively equipped apparatus for example supplies correct data and/or that an automated process can be carried out without the likelihood that unforeseeable events occur or actions are carried out as a result of erroneous detection which are not adequate to the situation.

It is a further advantage of the invention that it is possible to distinguish between foam or liquid contacting, wherein both the detection of a foam boundary and also the detection of the liquid boundary occur according to measuring approaches which are compatible with respect to metrology and circuitry.

BRIEF DESCRIPTION OF THE DRAWINGS

The method in accordance with the invention is now explained in closer detail by reference to schematic drawings of exemplary embodiments, which drawings do not limit the scope of the invention.

DETAILED DESCRIPTION OF THE PREFERRED EMBODIMENTS

Advantageous embodiments of the invention are described below, wherein said embodiments are provided as examples. They comprise both different formations of the overall invention, but also assemblies and individual parts of the invention. The described assemblies and individual parts of the various embodiments can principally be combined with each other, or the assemblies and individual parts of individual embodiments can be replaced by the assemblies and individual parts of other embodiments. The combinations formed in this case can lead to minor adjustments that are known to every person skilled in the art and will therefore not be described in closer detail, e.g. in order to enable an interaction or mutual engagement of the assemblies and individual parts.

Figure 1:
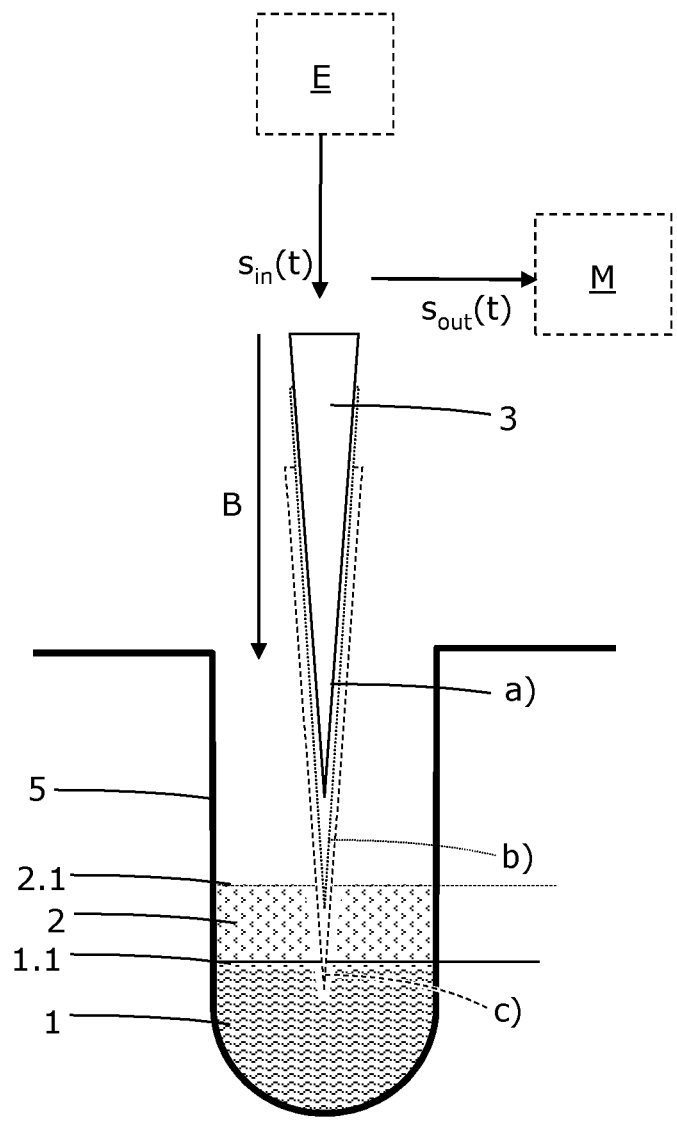
FIG. 1 shows a schematic illustration of the detection method according to the present invention, which shows a pipette used as a probe in three different feed motion depths a), b) and c)

The term phase boundary is used for boundaries between two or more media which have different dielectric constants. Gas-foam phase boundaries 2.1, foam-liquid phase boundaries 1.1, such as indicated in FIG. 1, and gas-liquid phase boundaries are concerned in particular.

The term module is used here in order to describe a functional group which is realised in form of hardware, software or as a combination of hardware and software.

The term "identifier" is used here for a code, a codeword, a signal, a memory entry which is made, or for a flag that is set.

Reference is made in numerous ways to devices in connection with the present invention. They preferably concern laboratory appliances and other systems, installations, apparatuses, handling centres and the like, which are equipped with means for determining a phase boundary. The apparatus 100 in accordance with the invention is an element or a component of such a laboratory device. A laboratory device can comprise several identical apparatuses 100 or several different apparatuses 100 of the invention.

The method in accordance with the invention is preferably formed in all embodiments for detecting the contacting of a probe 3 (e.g. a pipette or a needle used as a probe) with a medium in a (liquid) container 5 and for distinguishing whether contacting has occurred with a liquid 1 or with foam 2. Reference is made below to the use of pipettes, wherein other (pipette) tips, needles, small tubes and the like are suitable as probes 3 and can be used in all embodiments of the invention.

Reference is made below to the performance of a feed motion B. Such a feed motion B can describe a downward or an upward movement of the probe 3 in the container 5.

For the purpose of detection, a pipette 3 is preferably used which can be advanced in the direction of a foam boundary 2.1 and/or in the direction of a liquid boundary 1.1 into the container 5.

FIG. 1 shows a schematic illustration of the basic principle of the detection method of the present invention, wherein the pipette 3 is shown in three different feed motion depths along the feed motion direction B, namely a) before piercing the foam boundary 2.1; b) after piercing the foam boundary 2.1; and c) after piercing the liquid boundary 1.1. During the feed motion B of the pipette 3 in the direction of the foam boundary 2.1 and/or the liquid boundary 1.1, a periodic input signal $s_{in}(t)$ is applied to the pipette 3. Once the tip of the pipette 3 touches the surface 2.1 of foam 2 for example, the foam 2, together with the liquid 1 in the container 5, forms a part of the probe 3 forming the measurement electrode, or a measuring capacitance (also known as total capacitance) is obtained from the pipette 3, the air, the foam 2 and the liquid 1.

FIG. 1 also shows the fundamental elements of a first exemplary equivalent circuit diagram, wherein the illustrated equivalent circuit comprises an input signal generator E and a measuring apparatus M. The aforementioned input signal $s_{in}(t)$ is provided by the input signal generator E and produces a respective charging signal on the pipette 3, while the output signal $s_{out}(t)$ which is tapped from the probe 3 is processed by the measuring apparatus M.

These aspects are described in detail below by reference to specific embodiments.

Figure 2A:
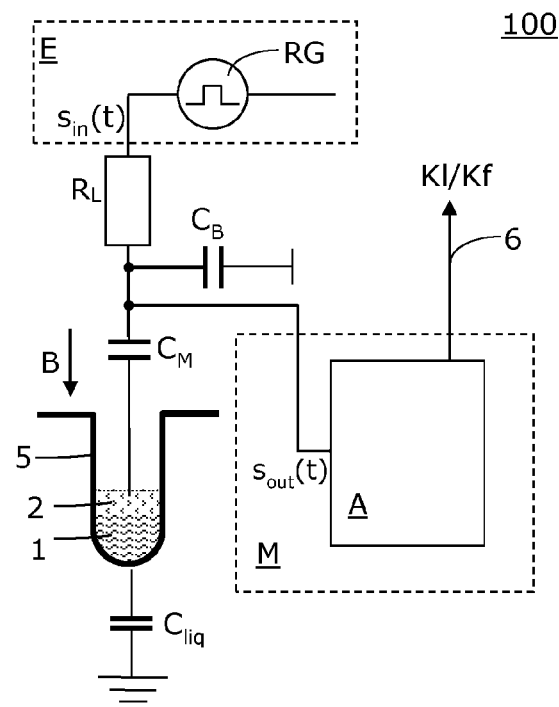
FIG. 2A shows a schematic circuit diagram of a first embodiment of a substantially capacitively operating apparatus, according to the present invention.

FIG. 2A shows a schematic circuit diagram of a first exemplary embodiment of the input signal generator E and the capacitively operating measuring apparatus M, which can be used in connection with the present invention. The pipette 3 is used as a probe and forms a capacitor together the foam/liquid surface, wherein the air forms the dielectric between the plates of said capacitor. The tip of the pipette 3 is used as the first part of a measuring capacitor with two capacitor plates, and the liquid surface 1.1 or foam surface 2.1 (depending on the situation) forms the second part with an interposed air dielectric. When the position of the pipette 3 is changed (by a movement B) the plate distance of the capacitor plates is also changed. Pipette 3 is therefore symbolised in FIG. 2A by two parallel capacitor plates and the respective capacitance is designated here as series capacitance $C_M$. The capacitance of the liquid 1, optionally combined with foam 2 in container 5, is designated as capacitance $C_{liq}$ and is also symbolised in FIG. 2A by two parallel capacitor plates, which are situated here beneath the container 5.

A basic capacitance $C_B$ is obtained (also symbolised in FIG. 2A by two parallel capacitor plates), which typically comprises the line capacitances, the probe capacitance and the capacitances of circuit parts which are disposed in the input signal generator E and in the evaluation circuit A. The basic capacitance $C_B$ is composed here of approximately 100 pF of cable capacitance, approximately 50 pF of circuit capacitance and approximately 2 pF of needle capacitance for example. The total capacitance $C_T$ (not shown) comprises both the basic capacitance $C_B$, the series capacitance $C_M$ and also the capacitive influences (known as capacitance $C_{liq}$) of the liquid 1 and/or the foam 2.

A sudden detectable change in the total capacitance $C_T$ occurs when the tip of the pipette 3 touches the liquid surface 1.1. This is also the case when the foam surface 2.1 is touched.

The apparatus 100 and/or the input signal generator E comprises a rectangular voltage generator RG (also known as rectangular pulse generator) for generating a periodic rectangular input signal $s_{in}(t)$. Instead of a rectangular voltage, another signal such as a periodic triangular input signal $s_{in}(t)$ or also charging and discharging by means of a constant current or the like can also be used.

The rectangular voltage generator RG can be regarded functionally as a part of an input signal generator E which generates the input signal $s_{in}(t)$. Said input signal $s_{in}(t)$ generates a respective charging signal via the charging resistance $R_L$ on the probe 3 (on the pipette 3), which is used in all embodiments as the measurement electrode. Specifically, said charging signal is obtained during the charging process on the aforementioned total capacitance $C_T$.

Figure 6:
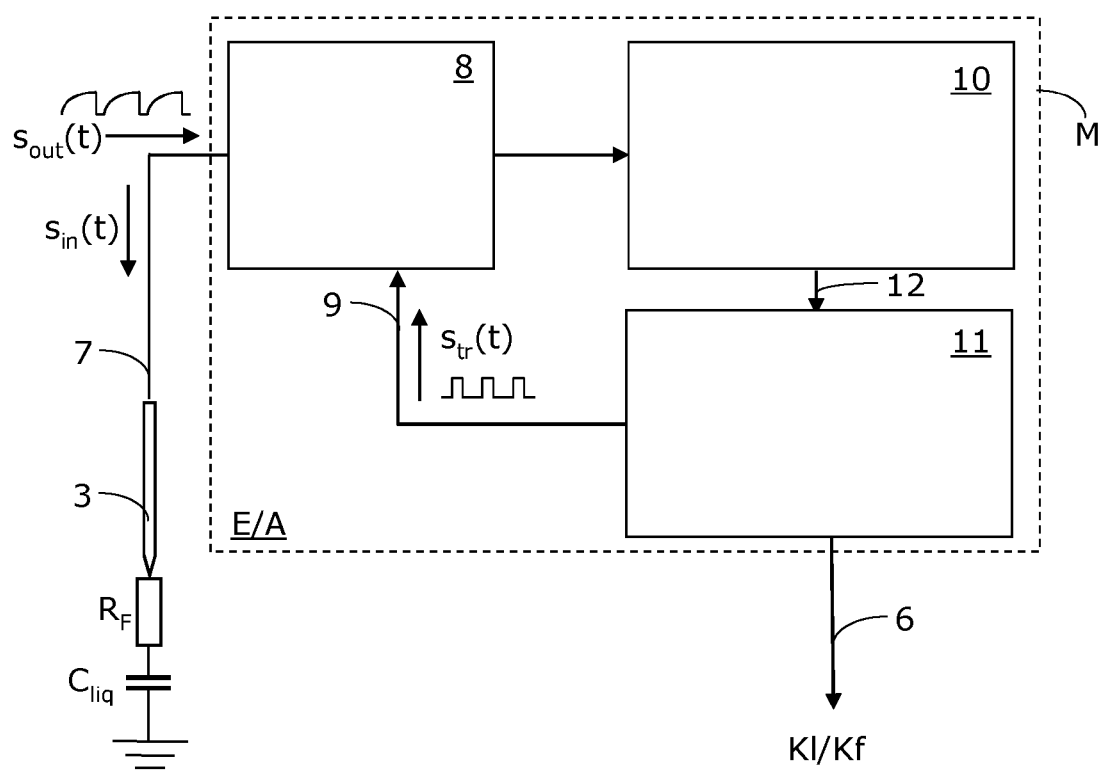
FIG. 6 shows a schematic circuit diagram of a further embodiment of an apparatus of the present invention.
Figure 7:
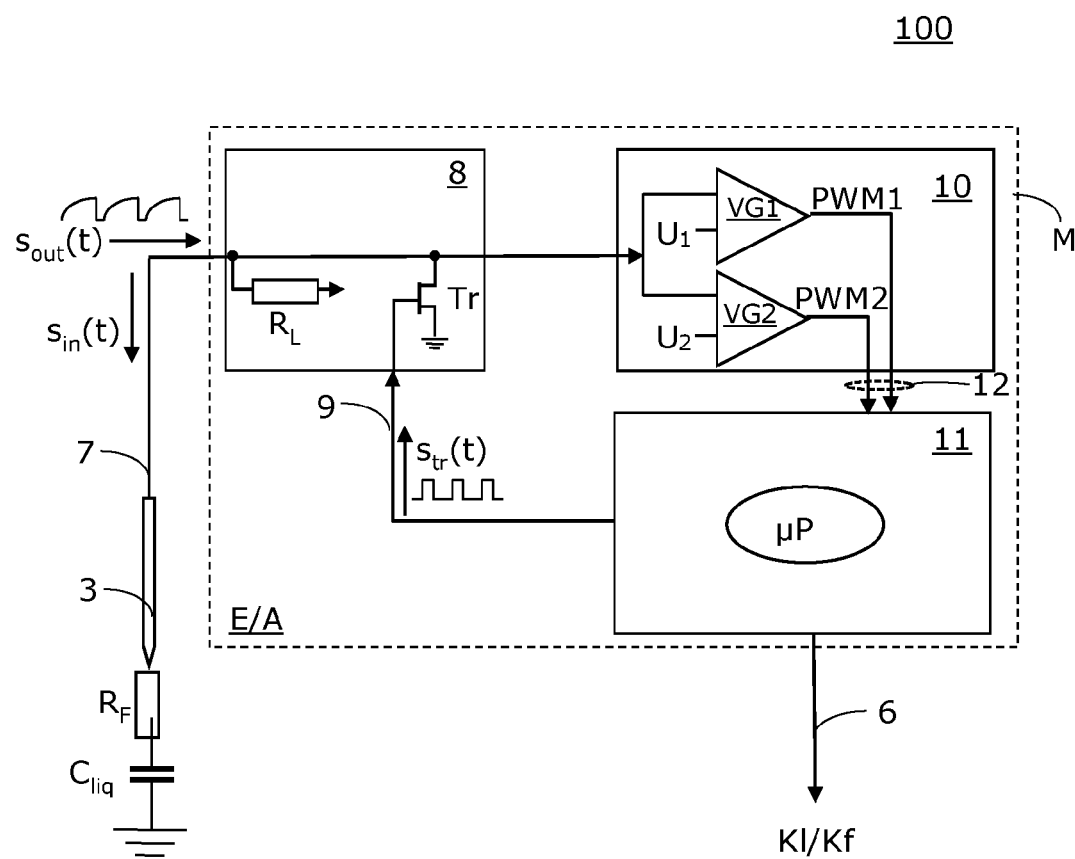
FIG. 7 shows a schematic circuit diagram of a further embodiment of an apparatus of the present invention, wherein said apparatus is based on the principle of FIG. 6.
Figure 8:
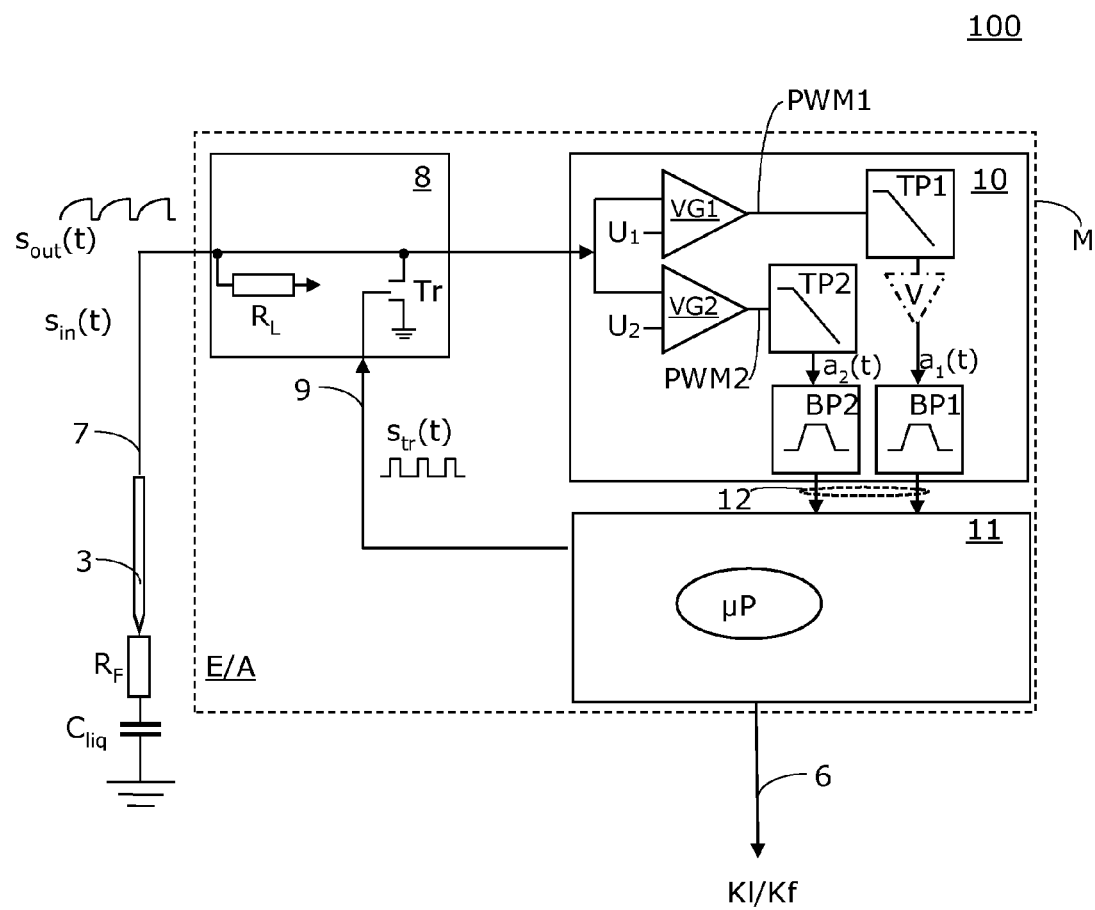
FIG. 8 shows a schematic circuit diagram of a further embodiment of an apparatus of the present invention, wherein said apparatus is based on the principle of FIGS. 6 and 7.

It is understood that other generally known types of voltage generators or current generators can also be used for the method in accordance with the invention, as shown in FIGS. 6, 7 and 8.

It is not absolutely necessary to generate a classic rectangular signal as the input signal $s_{in}(t)$. A signal could also be generated alternatively for example which approaches a rectangular signal. Other square-wave signals can also be used in all embodiments instead of rectangular pulses. All these signals and signal forms are designated here in summary as periodic input signals $s_{in}(t)$.

FIG. 2A shows by reference to an exemplary circuit diagram that during the charging process the total capacitance $C_T$ can be periodically charged and discharged via the (charging) resistance $R_L$ by means of the rectangular pulse generator RG.

While the input signal $s_{in}(t)$ is applied by the input signal generator E to the probe 3, or the total capacitance $C_T$ respectively, the output signal $s_{out}(t)$ of the probe 3 is processed/evaluated by means of an evaluation circuit A, as described below. Changes in the curve shape of the charging curves of the charging signals on the probe 3, or the total capacitance $C_T$ respectively, are of special interest. For this purpose, the evaluation circuit A can be connected by circuitry to the probe 3 in all embodiments.

The evaluation circuit A, or the measuring apparatus M respectively, can comprise in all embodiments an amplifier V for amplifying the output signal $s_{out}(t)$. An amplifier V can be used in all embodiments of FIGS. 6, 7 and 8 in the region after the low-pass filter TP1, because the comparator VG1 processes a signal which can be distinctly smaller than the signal which is processed by the comparator VG2. A respective amplifier V is shown in FIG. 8 by way of example.

Figure 2B:
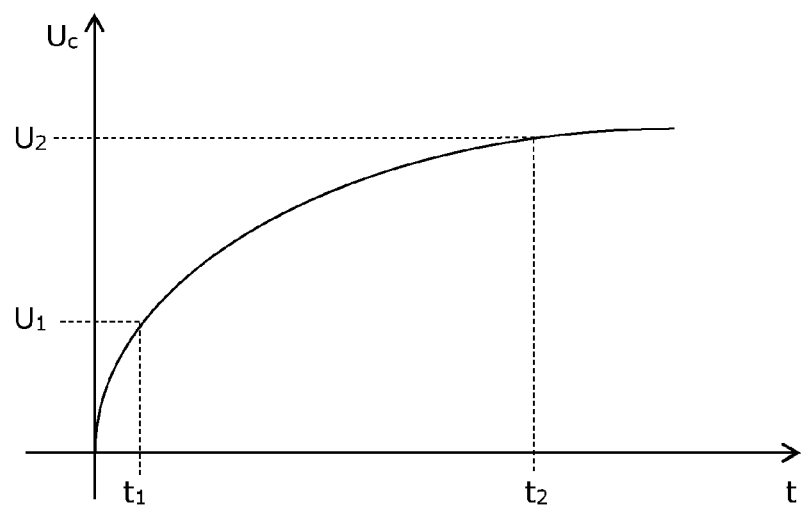
FIG. 2B shows a schematic voltage-time diagram of a charging curve, wherein an input signal generator of the apparatus according to FIG. 2A is used which predetermines in this case a periodic rectangular input signal (note: if the total capacitance were to be charged with a constant current then the charging curve of FIG. 2B would have a linear progression)

FIG. 2B shows a schematic voltage-time diagram of the charging curve (the charging signal) of the measuring apparatus M with the input signal generator E of FIG. 2A. The curve according to FIG. 2B concerns the typical charging curve of a capacitor. The charging behaviour, or the time progression of said charging curve respectively, is proportional to the product of the total capacitance $C_T$ and the resistance.

The charging and discharging process is repeated in accordance with the invention at a high cycle rate. The input signal generator E is preferably formed in all embodiments to provide the rectangular input signal $s_{in}(t)$ at a cycle rate which is greater than 10 kHz. The respective rectangular signal can preferably have a frequency of 100 kHz and more.

The evaluation of the output signal $s_{out}(t)$ within the scope of liquid level detection (which is referred to here as a further evaluation process P2) comprises the measurement/determination of a first charging time $t_1$ until reaching a first voltage $U_1$ and the measurement/determination of a second charging time $t_2$ until reaching a second voltage $U_2$, as shown in FIG. 2B.

As a result of the fact that a rectangular signal $s_{in}(t)$ is applied according to the invention, a discharging process of the total capacitance $C_T$ occurs after the charging process (which is shown in FIG. 2B by way of example). If only a liquid 1 is situated in the container 5, the total capacitance $C_T$ is completely discharged before a renewed charging process begins. This renewed charging process starts at zero again.

Figure 3:
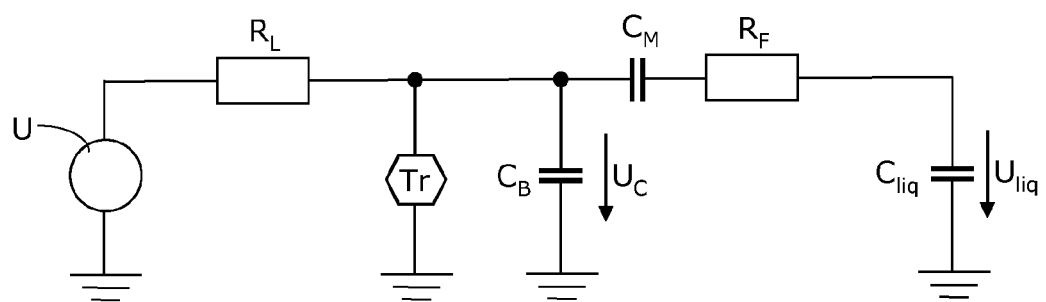
FIG. 3 shows a schematic equivalent circuit of a further embodiment of the present invention.

FIG. 3 shows a simplified equivalent circuit in order to enable the description of these processes. A voltage source U is shown on the left, which generates and applies a periodic rectangular signal for example during periodic actuation of a transistor Tr or any other discharging switch. The liquid 1 is symbolised in this simplified equivalent circuit by the capacitance $C_{liq}$ against ground. The foam 2 is represented in this simplified equivalent circuit as a series resistance $R_F$, which is disposed in series with the liquid capacitance $C_{liq}$ and the aforementioned series capacitance $C_M$. If no foam 2 is present in the container 5, $R_F=0$ applies. The discharging of the total capacitance $C_T$ is produced by a transistor Tr which is used as a discharging switch. A field-effect transistor can be used for example as the transistor Tr.

Figure 4:
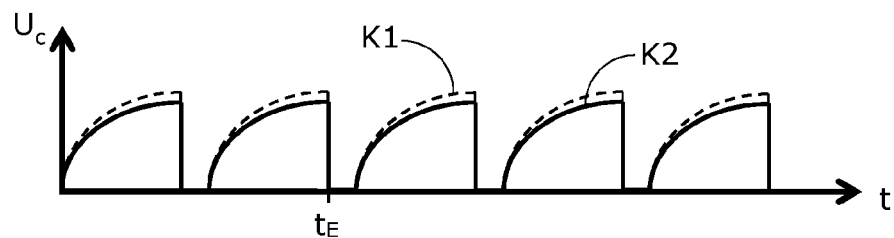
FIG. 4 shows a schematic voltage-time diagram in which the curve progression is shown with a probe not immersed in liquid (shown here as a curve progression K1 with a dashed line) and with a probe immersed in liquid (shown here as a curve progression K2 with an unbroken line)

During periodic charging and discharging, a curve progression according to FIG. 2B is obtained, wherein said curve progression is repeated periodically, as indicated in FIG. 4. The curve progression K1 in FIG. 4 represents the progression of the charging-discharging curve if the probe 3 is not situated in the liquid 1. The discharge time is designated with $t_E$. If the probe 3 dips into the liquid 1 which is situated in the container 5, the liquid capacitance $C_{liq}$ is added to the basic capacitance $C_B$. From a computational standpoint, the values of the two capacitances must be added in this case as follows: $C_T=C_{liq}+C_B$. The progression of the charging-discharging curve is thus changed, as is shown schematically in FIG. 4 by the curve progression K2. The immersion of the probe 5 into a liquid 1 can be detected by suitable evaluation of the difference of the two curve progressions K1 and K2 (e.g. by means of two comparators). The evaluation of the two curve progressions K1 and K2 can occur for example by generating and comparing pulse-width-modulated signals, wherein the pulse-width-modulated signal, when the probe 3 is not immersed, has a different pulse width than the pulse-width-modulated signal when the probe 3 is immersed. The question whether the pulse width is greater or smaller depends on the polarity of the series-connected comparator.

Figure 5:
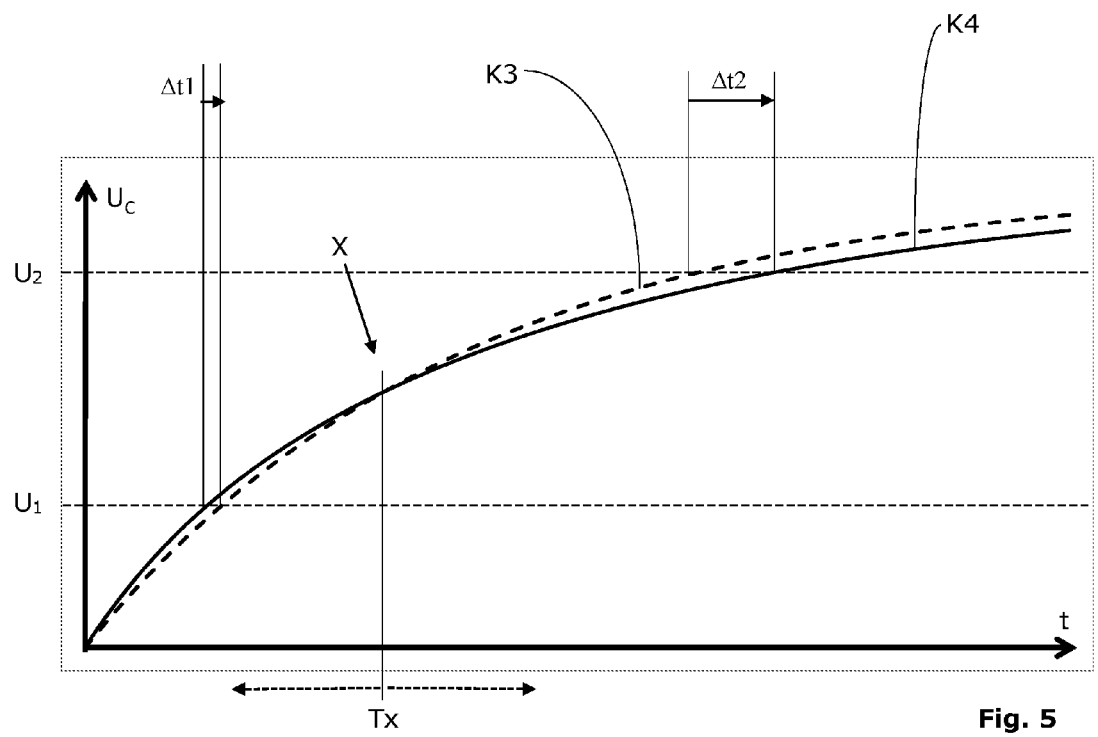
FIG. 5 shows a schematic voltage-time diagram with a probe not immersed in foam (shown here as a curve progression K3 with a dashed line) and with a probe immersed in foam (shown here as a curve progression K4 with an unbroken line) (note: in the case of a non-immersed probe the connection to the resistance $R_F$ in FIG. 3 would be interrupted)

If foam 2 is situated in the container 5, an inspection of the charging curves supplies a signal as shown in FIG. 5 by way of example. The curve progression K3 in FIG. 5 represents the progression of the charging curve if the probe 3 is not situated in the foam 2 (which is also designated here as the surfaced state). If the probe 3 dips into the foam 2 (which is also designated here as the immersed state) which is situated in the container 5 (curve K4), the series circuit consisting of the foam resistance $R_F$, the series capacitance $C_M$ ($C_M$ can be disregarded after the contact, it therefore corresponds to a short-circuit) and the liquid capacitance $C_{liq}$ is added to the basic capacitance $C_B$. If the discharge time $t_E$ is selected in a sufficiently short way, a specific residual charge remains in the liquid 1 due to the relatively high-resistance foam resistance $R_F$ after discharging, whereas the basic capacitance $C_B$ is discharged fully by the circuit. At the beginning of the next charging, a current thus flows at the beginning from the charge in $C_{liq}$ of the liquid back to the basic capacitance $C_B$ of the circuit. This current is added to the charging current of $R_L$. Current will flow again into the liquid 1 (point in time Tx in FIG. 5) only when the charging voltage of the basic capacitance $C_B$ reaches the same voltage level as the voltage of the liquid capacitance (i.e. only when $U_C=U_{liq}$).

This effect is utilised by the invention in that the evaluation circuit A preferably comprises two comparators VG1 and VG2 in all embodiments. In comparison with the signal K3 of the surfaced probe 3, the comparator VG1, whose switching threshold lies at $U_1$, switches earlier, and VG2, whose switching threshold lies at $U_2$, switches later. The time changes Δt1 and Δt2 are therefore of interest. The comparison of these time changes Δt1 and Δt2 allows making a statement on whether the medium touched by the probe 3 only consists of the liquid 1 or whether foam 2 was touched.

In this process, the pulse widths of the first comparator output signal PWM1 and the second comparator output signal PWM2 are of interest, especially the change Δt1 and Δt2 of the pulse widths of these comparator output signals PWM1, PWM2 when touching the medium. The change Δt1 of the first comparator output signal PWM1 can be multiplied by a predetermined factor k in such a way that the product, in the case of purely capacitive behaviour of the medium, corresponds to the change Δt2 of the second comparator output signal PWM2. This is the case when the probe 3 touches a somewhat well-conducting liquid 1. If foam 2 is situated on the liquid 1, the liquid capacitance $C_{liq}$, in the case of a suitable selection of the discharge time $t_E$ (see FIG. 4), cannot be fully discharged as a result of the relatively high impotence of the foam 2. This leads to the consequence that during the subsequent charging process a reverse current flows back into the basic capacitance $C_B$ at the beginning during the subsequent charging process. The flow of a reverse current has an effect especially at the beginning of the charging curve. The pulse-width change of the first comparator output signal PWM1 which is multiplied by the predetermined factor k can thus decrease in comparison with the pulse-width change of the second comparator output signal PWM2. The pulse-width change can even become negative. As a result of the suitable selection of the discharge time $t_E$ and the basic capacitance $C_B$, it is thus possible to distinguish whether the probe 3 is immersed in the liquid 1 or in the foam 2.

FIG. 5 shows an enlarged view of two exemplary curves. The curve progression K3 in FIG. 5 represents the progression of the charging curve if the probe 3 is not situated in the foam 2 (surfaced state). If the probe 3 is immersed into the foam 2, the residual charge of the preceding charging process in the total capacitance $C_T$ has an influence on the behaviour during the next charging process. The progression of the respective curve K4 is therefore slightly different than the progression of the curve K3. In simple terms, the curve K4 initially has a higher gradient than the curve K3. A point of intersection between the two curves K3 and K4 is obtained in a region X (see FIG. 5).

The following two conditions B1 and B2 can be derived from FIG. 5.

Condition B1: the output signal $s_{out}$ of the pipetting needle immersed in the foam (curve K4 in FIG. 5) rises in an initial region (time window less than Tx) more rapidly than the output signal $s_{out}$ of the pipetting needle that is not yet immersed (curve K3 in FIG. 5).

Condition B2: the output signal $s_{out}$ of the pipetting needle immersed in the foam (curve K4 in FIG. 5) rises in a region after the initial region (time window greater than Tx) more slowly than the output signal $s_{out}$ of the pipetting needle that is not yet immersed (curve K3 in FIG. 5).

The relative progression of the two curves K3 and K4 can be explained as follows. At the beginning of a charging cycle the liquid capacitance $C_{liq}$ still has a residual charge from the temporarily preceding charging cycle. This is caused on the one hand by the relatively high resistance of the foam $R_F$, and on the other hand by the fact that the discharge time was intentionally selected to be short in order to prevent complete discharging. That is why the liquid capacitance $C_{liq}$ is discharged first until the voltages $U_C$ and $U_{liq}$ reach the same voltage level (i.e., the following applies: $U_C = U_{liq}$). The current then flows in the positive direction. This leads to the point of intersection X at the point in time Tx of the two curves K3 and K4, as shown in FIG. 5.

The invention is thus based on the approach to not intentionally completely discharge the liquid capacitance $C_{liq}$ when foaming occurs. In other words, the circuit configuration of the apparatus 100 and the influenceable parameters (e.g. the discharge time) are selected in such a way that a residual charge always remains in the liquid capacitance $C_{liq}$ during discharging before the new charging cycle starts. A residual charge in the liquid 1 is thus intentionally used in order to obtain a signal progression in the immersed probe 3 in the foam 2 which can be reliably evaluated by the circuit A. The residual charge of the liquid capacitance $C_{liq}$ is a function of the resistance $R_F$ and the discharge time $t_E$.

The discharge time is thus one of the potential parameters which are preferably set in all embodiments of the apparatus 100 or which can be predetermined in other ways.

In accordance with the invention, the selection of the discharge time depends on the conductivity of the liquid 1, which means in preferred embodiments of the invention the setting or the definition of the discharge time is carried out by taking into account the conductivity of the liquid 1. Furthermore, two comparators (see VG1 and VG2 in FIG. 7) are preferably used in all embodiments in order to enable the detection of the presence of foam 2 in a reliable and reproducible manner.

It can be determined by using two comparators that a negative time delay Δt1 occurs to the left of the point of intersection X (i.e. in the initial region t<Tx) and a positive time delay Δt2 occurs to the right of the point of intersection X (i.e. in the region t>Tx). These two time delays Δt1 and Δt2 are schematically shown in FIG. 5. The time delay Δt2 is determined at a voltage U2 and the time delay Δt1 at a voltage U1 for example, which means that a comparator VG2 has a comparison threshold at voltage U2 and a comparator VG1 as a comparison threshold at voltage U1 (also see FIG. 7 and FIG. 8).

It can thus be derived from FIG. 5 that Δt1<0 and Δt2>0 must apply in order to assume the detection of foam. Furthermore, the following additional relationship applies optionally to all embodiments: Δt1<Δt2.

The foam detection, or the evaluation of the output signal $s_{out}(t)$ (or the comparator output signals PWM1, PWM2) respectively, is also designated here as (foam) evaluation process P1.

FIGS. 4 and 5 show that a positive time delay Δt2 always occurs during the immersion into the liquid 1 and also during the immersion into foam (in simple terms, because the curve K1 lies above the curve K2 in FIG. 4 and the curve K3 lies above the curve K4 in FIG. 5), which can be determined by the comparator VG2. A positive time delay Δt2 can also be measured in the other comparator VG1 during the immersion of the probe 3 into a liquid 1, which other comparator is used in all other embodiments for the purpose of foam detection within the scope of the (foam) evaluation process P1. The following relationship therefore applies to the two comparators VG1 and VG2: Δt2>0 and Δt1>0.

During the immersion of the probe 3 into foam 2 on the other hand, the following relationship applies to the two comparators VG1 and VG2: Δt1<0 and Δt2>0.

An evaluation circuit A is preferably used in all embodiments of the invention, which is formed in order to:

qualitatively evaluate a sudden change in the curve progression (note: two directly successive cycles do not provide sufficient measurement security) of the output signal $s_{out}(t)$ from $s_{out1}(t)$ to $s_{out2}(t)$ or vice versa (curves K4 and K3) (qualitative evaluation), and/or quantitatively evaluate a sudden change in the curve progression of the output signal $s_{out}(t)$ from $s_{out1}(t)$ to $s_{out2}(t)$ or vice versa (curves K4 and K3) (quantitative evaluation).

The complexity of the circuitry is high especially in the case of quantitative evaluation because very small signal changes are concerned which need to be detected and evaluated. The quantitative evaluation is aggravated by the fact that there are a number of influencing quantities which lead to distinct changes in the quantities to be measured and compared from detection case to detection case.

This evaluation can occur in all embodiments in an evaluation circuit A of the apparatus 100. As a result, the evaluation circuit A outputs an identifier Kl or it provides an identifier Kl which can be retrieved by another circuit or a computer. The identifier Kl indicates that a phase boundary between air and liquid 1 or between air and foam 2 was detected. Liquid 1 and foam 2 can be distinguished within the scope of an optional evaluation process P1. A respective evaluation process P1 can output an identifier Kf for example, wherein Kf=1 indicates the presence of foam 2 and Kf=0 indicates the absence of foam 2.

An evaluation circuit A is preferably used in all embodiments of the invention, which comprises at least two comparators VG1 and VG2 which are switched in parallel and which allow qualitative evaluation, as already indicated above. This means that these comparators VG1 and VG2 which are switched in parallel allow the correlation of two output signals $s_{out1}(t)$ and $s_{out2}(t)$ which are temporarily apart from one another. As an alternative to the time measurement until reaching a specific voltage, the evaluation circuit A can be configured in all embodiments in such a way that it evaluates the progression of current over time.

FIG. 6 shows the schematic circuit diagram of a further embodiment of the invention. The apparatus 100 comprises a measuring apparatus/circuit M in the case of this embodiment in which the evaluation circuit A and the input signal generator E are combined.

The measuring apparatus/circuit M comprises a common signal path 7, which is used for feeding the probe 3 and for tapping the signal from the probe 3. All embodiments can comprise a common signal path 7.

A shielded cable is preferably used in all embodiments as the signal path 7. A first circuit module 8 is used in this case for the periodic charging and discharging of the probe 3 and the other capacitances of the arrangement. The charging and discharging of the probe 3 is carried out by means of a periodic rectangular signal sequence for example, as already described above. Said rectangular signal sequence is generated in this case by a switching element Tr and is applied via the signal path 7 to the probe 3 (as shown in FIG. 3). The switching element Tr and the (charging) resistance $R_L$ can be part of the circuit module 8. The switching element Tr is supplied in the illustrated embodiment by a trigger signal $s_{tr}(t)$, which is applied for example by a signal path 9 to the circuit module 8. An exemplary trigger signal $s_{tr}(t)$ is shown in FIG. 6 adjacent to the signal path 9. Said signal produces the opening and closing of the switching element Tr. As long as the switching element Tr is closed there is a short-circuit to ground and a partial (in the case of foam detection) or complete (in the case of liquid detection) discharging of the capacitances occurs, as already described above. As soon as the switching element Tr opens again, a new charging process starts. This process is repeated with a very high cycle rate which lies in the range of ≥10 kHz and preferably in the range of ≥100 kHz. Said periodically repeating charging and discharging process generates a curved progression of the output signal $s_{out}(t)$, as shown in FIG. 6 above the signal path 7.

The measuring apparatus/circuit M preferably comprises in all embodiments an evaluation circuit A which is equipped with two comparators VG1, VG2 which are switched in parallel. In the embodiment of FIG. 6, these two comparators are situated in the second circuit module 10. The wiring of the two comparators VG1, VG2 in the second circuit module 10 is designed in such a way that a relative comparison of two output signals $s_{out1}(t)$, $s_{out2}(t)$ is possible. As a result of the correlation or the comparison of two output signals $s_{out1}(t)$, $s_{out2}(t)$, it is determined whether the following relation applies: $\Delta t1<0$ (first condition known as B1.) and $\Delta t2>0$ (second condition known as B2.).

The measuring apparatus/circuit M preferably comprises in all embodiments a control module 11, as shown in FIG. 6. Said control module 11 can be configured in such a way that it outputs an identifier Kf (Kf is an identifier in order to allow distinguishing foam 2 from liquid 1) if the described relation is present, i.e. if the first condition B1 and the second condition B2 are fulfilled. Said identifier Kf can be provided on an output 6 (as also in FIG. 2A). The aforementioned identifier Kl can also be provided on the output 6 or any other output.

The control module 11 is preferably supplied by the circuit module 10 with one or several signals, as symbolised in FIG. 6 by the signal path 12.

The control module 11 is preferably equipped in all embodiments with a processor µP (see FIG. 7) in order to process predefined processes and in order to allow decisions to be made and reactions to be triggered such as the output of the identifier Kf for distinguishing liquid 1 and foam 2, and/or the identifier Kl for the detection of an air-liquid or air-foam boundary.

The control module 11 can be formed in all embodiments in such a way that it assumes control of the charging and discharging process, as shown in FIG. 6 by the signal path 9 and the trigger signal $s_{tr}(t)$. The duration of the discharging process can preferably be influenced by the control module 11 in order to maintain a residual charge in the capacitance $C_{liq}$ which is required for reliable foam detection.

FIG. 7 shows a schematic circuit diagram of a further embodiment of an apparatus 100 of the present invention, wherein said apparatus 100 is based on the principle of FIG. 6.

The circuit module 8 comprises a transistor Tr, which is used as a switching element. Said transistor Tr is switched in this case by the trigger signal $s_{tr}(t)$, which is provided by the control module 11. The circuit module 8 can further comprise the (charging) resistance $R_L$, as schematically indicated (it would also be possible to use a constant current source instead of $R_L$). The signal path 7 is through-connected in the illustrated example up to the circuit module 10 in order to supply the two comparators VG1 and VG2 in parallel. This means that the two comparators VG1 and VG2 are switched in parallel. The first comparator VG1 compares the output signal $s_{out}(t)$ with a voltage U1 (also see FIG. 5) and the second comparator VG2 compares the output signal $s_{out}(t)$ with a voltage U2, wherein U1<U2. Each comparator can be provided in outgoing series with a low-pass filter and/or further circuit blocks (e.g. an amplifier V). A pulse-width-modulated signal (PWM1 and PWM2) is provided on the output side (on the right-hand side of the comparators VG1, VG2 in FIG. 7). These two comparator output signals PWM1, PWM2 are processed by the control module 11 in order to check whether the conditions B1.=$\Delta t1<0$ and B2.=$\Delta t2>0$ are fulfilled. If these conditions B1. and B2. are fulfilled, the control module 11 outputs the identifier Kf=1 for example in order to thus indicate the detection of foam 2.

Further details are explained below, which can be considered in each of the embodiments. Preferably, an individual charging curve is not compared directly with the charging curve that follows next in time. The change in the charging curve and thus the respective pulse-width change are relatively small. It can therefore only be measured by a conventional processor µP (which can be part of the circuit 11) only with much effort. Furthermore, the signal-to-noise ratio may be unfavourable under certain circumstances.

Averaging over several charging curves is therefore preferably carried out in all embodiments, as described below. A respective circuit example based on FIGS. 6 and 7 is shown in FIG. 8. The explanations made with respect to FIGS. 6 and 7 can be applied here analogously. Each of the two PWM signals PWM1 and PWM2 is converted via one low-pass filter TP1, TP2 each into an analog signal $a_1(t)$, $a_2(t)$ each. These low-pass filters TP1, TP2 are situated in the region behind the comparators VG1 and VG2, as shown in FIG. 8. The cycle frequency is also completely filtered out of the signals by the low-pass filters TP1, TP2. An amplifier can optionally be arranged after the low-pass filter TP 1 for example, as illustrated in FIG. 8 by a circuit symbol bounded by a dashed line, or after the bandpass filter BP1. The thus produced analog signals $a_1(t)$, $a_2(t)$ also change their value during the immersion or surfacing of the probe 3 only in a very low voltage range so that direct evaluation of these changes is only possible with high-resolution analog-to-digital converters.

In accordance with the invention, the voltage change is preferably evaluated/processed and the offset is masked out, because it is much greater (determined by the total capacitance $C_T$) and an amplifier directly connected in series would overmodulate even at low amplification. The direct voltage component of the analog signals $a_1(t)$, $a_2(t)$ can be decoupled in all embodiments via a respective series-connected bandpass filter BP1, BP2 through a series-connected capacitance and the useful signal can be amplified at the same time. The signal of the comparator VG1 is preferably amplified by a fixed factor (factor k) more, so that in the case of pure liquid contact two equally large and equally polarised signals are generated at the output of the two bandpass filters BP1, BP2 (see FIG. 8).

In contact with foam 2 on the other hand, the output signal $a_1(t)$ to BP 1, which is used for foam recognition, is mostly reversely poled.

The total capacitance $C_T$ changes only very slowly when the probe 3 moves downwardly. An output signal is therefore hardly produced on the two bandpass filters BP1, BP2, unless the probe 3 is moved very rapidly. Once the probe 3 enters the medium, a highly rapid change in capacitance occurs, which can now clearly be detected by means of the two bandpass filters BP1, BP2. The output signal of the bandpass filter BP2 is advantageously evaluated for determining whether the probe 3 has entered a medium or has surfaced therefrom, which bandpass filter BP2 processes the signal PWM2 which originates from the comparator VG2 which operates with the higher reference voltage $U_2$. The evaluation of the output signal of the bandpass filter BP2 occurs in that it is determined whether said output signal reaches a specific minimum value (threshold value).

Said minimum value (threshold value) is preferably selected in all embodiments depending on the conductivity of the liquid 1. The comparison which is required during evaluation can occur for example via a further comparator (not shown) or it can be carried out for example by the processor μP. If such a further comparator is used, then it is situated for example on the output side of the bandpass filter BP2. If the processor μP carries out the comparison, the signal or signals are transmitted via the signal path 12 to the processor μP.

Only at this point, after the recognition of a detection, will the output signal of the other bandpass filter BP1 (i.e. the PWM signal PWM1 generated with the lower reference voltage) be evaluated in order to compare it with the other output signal of the bandpass filter BP2. If it is in phase opposition, it can clearly be assumed that foam detection is concerned. If it is in equal phase but considerably lower it can also be interpreted as foam detection. This can be the case for example in highly conductive liquids 1 where the crossover point X is situated beneath the two comparator levels U1 and U2 (see FIG. 5). If both output signals appear virtually similarly, pure liquid contact can be assumed.

The apparatus 100 can output an identifier Kl and/or Kf in all embodiments for example, or it can provide an identifier Kl and/or Kf which can be retrieved by another circuit or a computer. The provision of the respective identifiers is symbolised in FIG. 2A and in FIGS. 6, 7 and 8 by the arrow 6 with the reference symbol Kl/Kf. Depending on the configuration, the apparatus 100 can also distinguish whether the probe 3 was immersed in liquid 1 or in foam 2. In this case, the apparatus 100 can output in all embodiments an identifier Kf=0 for liquid 1 and Kf=1 for foam 2, or it can provide a respective identifier Kl. The provision of the respective identifier Kf is optional.

These identifiers can be provided in all embodiments on a common output 6 or also on separate outputs of the apparatus 100.

The apparatus 100 can also contain in all embodiments an analog electrical circuit and/or a digital circuit with a processor.

If the contact of the probe 3 with the foam 2 was recognised, a further "examination" can optionally follow in all embodiments while the probe 3 is further moved in the previous direction in order to enable the recognition of a subsequent liquid boundary 1.1 (which lies beneath the foam 2 during the downward movement or lies above the foam 2 during the upward movement).

The concept of the circuit on which all circuits according to the drawings are based can also be reversed in all embodiments of the invention. In these drawings, the liquid container 5 is grounded and signals (known as input signals $s_{in}(t)$) are applied to the probe 3. In the reversal of the concept of the circuit, the probe 3 would be grounded and signals (known as input signals $s_{in}(t)$) would be applied to the liquid container 5. In this case, it may be necessary to provide certain adjustments on the part of the circuits E and A.

Circuits are also alternatively possible which do not relate to ground, as described above. Such an alternative circuit can comprise a capacitive voltage divider in the form of a measuring bridge. Circuits are also possible which evaluate the progression of a current curve in a rectangular input signal $s_{in}(t)$, or which evaluate a voltage curve in a predetermined current. It is further possible to evaluate the residual voltage in the total capacitance $C_T$ after its discharging and prior to the respectively following renewed charging. Such circuits are also used for realising or implementing the present invention.

| List of reference numerals | |
|---|---|
| Liquid | 1 |
| Liquid boundary | 1.1 |
| Foam | 2 |
| Foam boundary | 2.1 |
| Probe | 3 |
| (Liquid) container | 5 |
| Output | 6 |
| Signal path | 7 |
| First circuit module | 8 |
| Signal path | 9 |
| Second circuit module | 10 |
| Control module | 11 |
| Signal path | 12 |
| Apparatus | 100 |
| Evaluation circuit | A |
| Analog signals | $a_1(t)$, $a_2(t)$ |
| Movement | B |
| First bandpass filter | BP1 |
| Second bandpass filter | BP2 |
| First time delay/change of the first output signal | $\Delta t1$ |
| Second time delay/change of the second output signal | $\Delta t2$ |
| Input signal generator | E |
| Capacitance of the liquid | $C_{liq}$ |
| Basic capacitance | $C_B$ |
| Series capacitance | $C_M$ |
| Total capacitance | $C_T$ |
| Factor | K |
| Curves, curve progressions | K1, K2, K3, K4 |
| Identifier for air-liquid and air-foam | Kl |
| Identifier for distinguishing foam and liquid | Kf |
| Measuring apparatus/circuit | M |
| (Foam) evaluation process | P1 |
| Further evaluation process | P2 |
| Pulse-width-modulated signals/comparator | PWM1, PWM2 |

-continued

| List of reference numerals | |
|---|---|
| output signals | |
| Rectangular voltage generator | RG |
| Foam resistance | $R_F$ |
| (Charging) resistance | $R_L$ |
| Input signal | $s_{in}(t)$ |
| Output signal (general) | $s_{out}(t)$ |
| First output signal (for surfaced probe) | $s_{out1}(t)$ |
| Second output signal (for immersed probe) | $s_{out2}(t)$ |
| Trigger signal | $s_{tr}(t)$ |
| Time | t |
| Discharging time | $t_E$ |
| First low-pass filter | TP1 |
| Second low-pass filter | TP2 |
| Transistor (FET) | Tr |
| Point of time at point of intersection X | Tx |
| Voltage source | U |
| First voltage/first reference signal | $U_1$ |
| Second voltage/second reference signal | $U_2$ |
| Voltage on the capacitance | $U_C$ |
| Voltage on the liquid capacitance | $U_{liq}$ |
| Processor | μP |
| Amplifier | V |
| First comparator | VG1 |
| Second comparator | VG2 |
| Point of intersection | X |

The invention claimed is:

1. A method for detecting a foam boundary (2.1) in a container (5) of an apparatus (100) by means of a capacitively operating measuring apparatus (M) with a probe (3) which can be moved, wherein at least one output signal ($s_{out}(t)$) is processed by the measuring apparatus (M), wherein the method comprises the following steps which are carried out while performing an upward or downward movement (B) of the probe (3) in the container (5);
   a) performing a charging process by predetermining an input signal ($s_{in}(t)$);
   b) providing the at least one output signal ($s_{out1}(t)$, $s_{out2}(t)$) on a first comparator (VG1) and on a second comparator (VG2), wherein the first comparator (VG1) is formed to provide a first comparator output signal (PWM1) if the at least one output signal ($s_{out1}(t)$, $s_{out2}(t)$) reaches a first reference voltage ($U_1$), and wherein the second comparator (VG2) is formed to provide a second comparator output signal (PWM2) if the at least one output signal ($s_{out1}(t)$, $s_{out2}(t)$) reaches a second reference voltage ($U_2$) which is greater than the first reference voltage ($U_1$);
   c) discharging the probe (3);
   d) repeating the steps a) to c);
   wherein within a scope of an evaluation process (P1) a residual voltage in a total capacitance ($C_T$) is evaluated after each discharging and prior to the respectively following renewed charging process based on the first comparator output signal (PWM1) and the second comparator output signal (PWM2).

2. The method according to claim 1, wherein the first comparator output signal (PWM1) and the second comparator output signal (PWM2) are correlated with one another within the scope of the evaluation process (P1) in order to determine B1 whether the output signal ($s_{out1}(t)$) of the surfaced probe (3) rises more rapidly in an initial range (<Tx) than the output signal ($s_{out2}(t)$) of the immersed probe (3), and
   B2 whether the output signal ($s_{out1}(t)$) rises more slowly in a range after the initial range (<Tx) than the output signal ($s_{out2}(t)$), and output of a detection (Kf) of a foam boundary (2.1) if the conditions B1 and B2, are fulfilled.

3. The method according to claim 2, wherein the steps a) to d) are carried out several times while performing the upward or downward movement (B) of the probe (3) until the conditions B1 and B2 are fulfilled.

4. The method according to claim 3, wherein the steps a) to d) are carried out at a cycle rate which is greater than 10 kHz.

5. The method according to claim 3, wherein the steps a) to d) are carried out at a cycle rate which is greater than 100 kHz.

6. The method according to claim 1, wherein the first comparator output signal (PWM1) and the second comparator output signal (PWM2) are provided by using two comparators (VG1, VG2) switched in parallel and are correlated by a control module (11).

7. The method according to claim 1, wherein the first comparator output signal (PWM1) and the second comparator output signal (PWM2) concern pulse-width-modulated signals, which are correlated in respect of circuitry by further circuit blocks which are arranged on an output side of the comparators (VG1, VG2).

8. The method according to claim 1, wherein the first comparator output signal (PWM1) is supplied to a first low-pass filter (TP1) and the second comparator output signal (PWM2) is supplied to a second low-pass filter (TP2) in order to obtain a first analog signal ($a_1(t)$) and a second analog signal ($a_2(t)$).

9. The method according to claim 8, wherein the first analog signal ($a_1(t)$) is processed by means of a first bandpass filter (BP1) and the second analog signal ($a_2(t)$) is processed by means of a second bandpass filter (BP2), and the output signals of these bandpass filters (BP1, BP2) are correlated by means of circuitry.

10. A capacitively operating apparatus (100), comprising:
   a container (5),
   a probe (3) which can be moved into the container (5) and/or out of the container (5),
   an input signal generator (E) which can be connected to the probe (3) in order to provide an input signal ($s_{in}(t)$) which produces a charging-discharging process in the probe (3),
   a measuring apparatus (M) which can be connected to the probe (3) in order to tap at least one output signal ($s_{out}(t)$, $s_{out1}(t)$, $s_{out2}(t)$) from the probe (3) during the charging-discharging process, characterized in that
   the probe (3) is periodically chargeable and dischargeable during the charging-discharging process,
   the at least one output signal ($s_{out}(t)$, $s_{out1}(t)$, $s_{out2}(t)$) corresponds to the time progression of a charging/discharging curve (K1, K2), which is produced by the periodic charging and discharging of a total capacitance ($C_T$),
   the apparatus (100) comprises a circuit module (10, 11) with two comparators (VG1, VG2), which are formed to provide a first comparator output signal (PWM1) and a second comparator output signal (PWM2) from the at least one output signal ($s_{out}(t)$, $s_{out1}(t)$, $s_{out2}(t)$),
   wherein the circuit module (10, 11) is adapted to evaluate a residual voltage in the total capacitance ($C_T$) after each discharging and prior to the respectively following renewed charging process based on the first comparator output signal (PWM1) and the second comparator output signal (PWM2) within the scope of an evaluation process (P1).

11. The apparatus (100) according to claim 10, wherein the two comparators (VG1, VG2) are switched in parallel, wherein the first comparator (VG1) is formed to provide the first comparator output signal (PWM1) if the at least one output signal ($s_{out}(t)$, $s_{out1}(t)$, $s_{out2}(t)$) reaches a first reference voltage ($U_1$), and wherein the second comparator (VG2) is formed to provide the second comparator output signal (PWM2) if the at least one output signal ($s_{out}(t)$, $s_{out1}(t)$, $s_{out2}(t)$) reaches a second reference voltage ($U_2$), wherein the second reference voltage ($U_2$) is greater than the first reference voltage ($U_1$).

12. The apparatus (100) according to claim 11, wherein each of the two comparators (VG1, VG2) is formed for providing a pulse-width-modulated output signal (PWM1, PWM2) each, and that said pulse-width-modulated output signals (PWM1, PWM2) can be correlated with one another by a control module (11).

13. The apparatus (100) according to claim 11, wherein each of the two comparators (VG1, VG2) is formed for providing a pulse-width-modulated output signal (PWM1, PWM2) each, and that said pulse-width-modulated output signals (PWM1, PWM2) can be correlated with one another by further switching elements (TP1, TP2, BP1, BP2).

14. The apparatus (100) according to claim 11, wherein the input signal generator (E) provides the input signal ($s_{in}(t)$) at a cycle rate which is greater than 10 kHz.

15. The apparatus (100) according to claim 10, including a capacitive voltage divider in form of a measuring bridge.

16. The apparatus (100) according to claim 11, wherein the input signal generator (E) provides the input signal ($s_{in}(t)$) at a cycle rate which is greater than 100 kHz.

* * * * *